United States Patent
Dunlevy et al.

(10) Patent No.: US 10,108,954 B2
(45) Date of Patent: Oct. 23, 2018

(54) SYSTEM AND METHOD FOR CRYPTOGRAPHICALLY VERIFIED DATA DRIVEN CONTRACTS

(71) Applicant: PokitDok, Inc., San Mateo, CA (US)

(72) Inventors: Tim Dunlevy, San Mateo, CA (US); Theodore C. Tanner, Jr., San Mateo, CA (US)

(73) Assignee: PokitDok, Inc., San Mateo, CA (US)

( * ) Notice: Subject to any disclaimer, the term of this patent is extended or adjusted under 35 U.S.C. 154(b) by 0 days.

(21) Appl. No.: 15/237,415

(22) Filed: Aug. 15, 2016

(65) Prior Publication Data

US 2017/0372300 A1 Dec. 28, 2017

Related U.S. Application Data

(60) Provisional application No. 62/354,561, filed on Jun. 24, 2016.

(51) Int. Cl.
| | |
|---|---|
| *G06Q 20/36* | (2012.01) |
| *G06F 19/00* | (2018.01) |
| *G16H 10/00* | (2018.01) |

(52) U.S. Cl.
CPC ............ *G06Q 20/36* (2013.01); *G06F 19/00* (2013.01); *G06Q 20/363* (2013.01); *G16H 10/00* (2018.01); *G06Q 2220/00* (2013.01)

(58) Field of Classification Search
CPC ... G06Q 20/36; G06Q 20/085; H04L 63/0807
USPC .......................................................... 705/2
See application file for complete search history.

(56) References Cited

U.S. PATENT DOCUMENTS

| | | |
|---|---|---|
| 5,872,021 A | 2/1999 | Matsumoto et al. |
| 6,546,428 B2 | 4/2003 | Baber et al. |
| 7,386,565 B1 | 6/2008 | Singh et al. |
| 7,917,378 B2 | 3/2011 | Fitzgerald et al. |
| 7,917,515 B1 | 3/2011 | Lemoine |
| 7,970,802 B2 | 6/2011 | Ishizaki |
| 7,992,153 B2 | 8/2011 | Ban |
| 8,073,801 B1 | 12/2011 | Von Halle et al. |
| 8,095,975 B2 | 1/2012 | Boss et al. |
| 8,103,667 B2 | 1/2012 | Azar et al. |
| 8,103,952 B2 | 1/2012 | Hopp |
| 8,203,562 B1 | 6/2012 | Alben et al. |

(Continued)

FOREIGN PATENT DOCUMENTS

| | | |
|---|---|---|
| GB | 2478440 | 10/2013 |
| WO | WO 2012/122065 | 9/2012 |

OTHER PUBLICATIONS

Ahlswede et al., *Network Information Flow*, IEEE Transactions on Information Theory, vol. 46, No. 4; Jul. 2000 (13 pgs.).

(Continued)

*Primary Examiner* — Hiep V Nguyen
(74) *Attorney, Agent, or Firm* — DLA Piper LLP (US)

(57) ABSTRACT

A system and method are disclosed that methodologies concerning cryptographically verified blockchain-based contract data inputs and off-chain side-effects. The system and method provide a deterministic and cryptographically verifiable chain of transactions, recorded on a blockchain (distributed ledger) system. This system provides an irrefutable public accounting of the transactions involved in incorporating on-chain contract execution with off-chain data and side-effects (resource actions).

20 Claims, 15 Drawing Sheets

(56) References Cited

U.S. PATENT DOCUMENTS

| | | |
|---|---|---|
| 8,229,808 B1 | 7/2012 | Heit |
| 8,286,191 B2 | 10/2012 | Amini et al. |
| 8,359,298 B2 | 1/2013 | Schacher et al. |
| 8,364,501 B2 | 1/2013 | Rana et al. |
| 8,417,755 B1 | 4/2013 | Zimmer |
| 8,495,108 B2 | 7/2013 | Nagpal et al. |
| 8,515,777 B1 | 8/2013 | Rajasenan |
| 8,817,665 B2 | 8/2014 | Thubert et al. |
| 8,984,464 B1 | 3/2015 | Mihal et al. |
| 9,165,045 B2 | 10/2015 | Mok et al. |
| 9,208,284 B1 | 12/2015 | Douglass |
| 2002/0022973 A1 | 2/2002 | Sun et al. |
| 2002/0038233 A1 | 3/2002 | Shubov et al. |
| 2002/0165738 A1 | 11/2002 | Dang |
| 2003/0055668 A1 | 3/2003 | Saran et al. |
| 2003/0097359 A1 | 5/2003 | Ruediger |
| 2003/0171953 A1 | 9/2003 | Narayanan et al. |
| 2003/0217159 A1 | 11/2003 | Schramm-Apple et al. |
| 2003/0233252 A1 | 12/2003 | Haskell et al. |
| 2004/0143446 A1 | 7/2004 | Lawrence |
| 2005/0010452 A1 | 1/2005 | Lusen |
| 2005/0071189 A1 | 3/2005 | Blake et al. |
| 2005/0102170 A1 | 5/2005 | Lefever et al. |
| 2005/0137912 A1 | 6/2005 | Rao et al. |
| 2005/0152520 A1 | 7/2005 | Logue |
| 2005/0182780 A1 | 8/2005 | Forman et al. |
| 2005/0222912 A1 | 10/2005 | Chambers |
| 2006/0036478 A1 | 2/2006 | Aleynikov et al. |
| 2006/0074290 A1 | 4/2006 | Chen et al. |
| 2006/0089862 A1 | 4/2006 | Anandarao et al. |
| 2006/0129428 A1 | 6/2006 | Wennberg |
| 2006/0136264 A1 | 6/2006 | Eaton et al. |
| 2007/0113172 A1 | 5/2007 | Behrens et al. |
| 2007/0118399 A1 | 5/2007 | Avinash et al. |
| 2007/0156455 A1 | 7/2007 | Tarino et al. |
| 2007/0174101 A1 | 7/2007 | Li et al. |
| 2007/0180451 A1 | 8/2007 | Ryan et al. |
| 2007/0214133 A1 | 9/2007 | Liberty et al. |
| 2007/0233603 A1 | 10/2007 | Schmidgall et al. |
| 2007/0260492 A1 | 11/2007 | Feied et al. |
| 2007/0276858 A1 | 11/2007 | Cushman et al. |
| 2007/0288262 A1 | 12/2007 | Sakaue et al. |
| 2008/0013808 A1 | 1/2008 | Russo et al. |
| 2008/0082980 A1 | 4/2008 | Nessland et al. |
| 2008/0091592 A1 | 4/2008 | Blackburn et al. |
| 2008/0126264 A1 | 5/2008 | Tellefsen et al. |
| 2008/0133436 A1 | 6/2008 | Di Profio |
| 2008/0288292 A1 | 11/2008 | Bi et al. |
| 2008/0295094 A1 | 11/2008 | Korupolu et al. |
| 2008/0319983 A1 | 12/2008 | Meadows |
| 2009/0083664 A1 | 3/2009 | Bay |
| 2009/0125796 A1 | 5/2009 | Day et al. |
| 2009/0192864 A1 | 7/2009 | Song et al. |
| 2009/0198520 A1 | 8/2009 | Piovanetti-Perez |
| 2009/0300054 A1 | 12/2009 | Fisher et al. |
| 2009/0307104 A1 | 12/2009 | Weng |
| 2009/0313045 A1 | 12/2009 | Boyce |
| 2010/0076950 A1 | 3/2010 | Kenedy et al. |
| 2010/0082620 A1 | 4/2010 | Jennings, III et al. |
| 2010/0088108 A1 | 4/2010 | Machado |
| 2010/0088119 A1 | 4/2010 | Tipirneni |
| 2010/0138243 A1 | 6/2010 | Carroll |
| 2010/0217973 A1 | 8/2010 | Kress et al. |
| 2010/0228721 A1 | 9/2010 | Mok et al. |
| 2010/0295674 A1 | 11/2010 | Hsieh et al. |
| 2010/0332273 A1 | 12/2010 | Balasubramanian et al. |
| 2011/0015947 A1 | 1/2011 | Erry et al. |
| 2011/0055252 A1 | 3/2011 | Kapochunas et al. |
| 2011/0071857 A1 | 3/2011 | Malov et al. |
| 2011/0137672 A1 | 6/2011 | Adams et al. |
| 2011/0218827 A1 | 9/2011 | Kennefick et al. |
| 2011/0270625 A1 | 11/2011 | Pederson et al. |
| 2012/0011029 A1 | 1/2012 | Thomas |
| 2012/0035984 A1 | 2/2012 | Srinivasa et al. |
| 2012/0078940 A1 | 3/2012 | Kolluri et al. |
| 2012/0130736 A1 | 5/2012 | Dunston et al. |
| 2012/0158429 A1 | 6/2012 | Murawski et al. |
| 2012/0158750 A1 | 6/2012 | Faulkner et al. |
| 2012/0173279 A1 | 7/2012 | Nessa et al. |
| 2012/0245958 A1 | 9/2012 | Lawrence et al. |
| 2012/0246727 A1 | 9/2012 | Elovici et al. |
| 2012/0290320 A1 | 11/2012 | Kurgan et al. |
| 2012/0290564 A1 | 11/2012 | Mok et al. |
| 2013/0030827 A1 | 1/2013 | Snyder et al. |
| 2013/0044749 A1 | 2/2013 | Eisner et al. |
| 2013/0085769 A1 | 4/2013 | Jost et al. |
| 2013/0138554 A1 | 5/2013 | Nikankin et al. |
| 2013/0166552 A1 | 6/2013 | Rozenwald et al. |
| 2013/0204940 A1 | 8/2013 | Kinsel et al. |
| 2013/0304903 A1 | 11/2013 | Mick et al. |
| 2014/0046931 A1 | 2/2014 | Mok et al. |
| 2014/0056243 A1 | 2/2014 | Pelletier et al. |
| 2014/0059084 A1 | 2/2014 | Adams et al. |
| 2014/0088981 A1 | 3/2014 | Momita |
| 2014/0136233 A1 | 5/2014 | Atkinson et al. |
| 2014/0222482 A1 | 8/2014 | Gautam et al. |
| 2014/0244300 A1 | 8/2014 | Bess et al. |
| 2014/0278491 A1 | 9/2014 | Weiss |
| 2014/0358578 A1 | 12/2014 | Ptachcinski |
| 2014/0358845 A1 | 12/2014 | Mundlapudi et al. |
| 2015/0095056 A1 | 4/2015 | Ryan et al. |
| 2015/0112696 A1 | 4/2015 | Kharraz Tavakol |
| 2015/0142464 A1 | 5/2015 | Rusin et al. |
| 2015/0199482 A1 | 7/2015 | Corbin et al. |
| 2015/0332283 A1 | 11/2015 | Witchey |
| 2016/0028552 A1* | 1/2016 | Spanos ............... H04L 9/3297 713/178 |
| 2016/0055205 A1 | 2/2016 | Jonathan et al. |
| 2016/0253679 A1 | 9/2016 | Venkatraman et al. |
| 2016/0261411 A1* | 9/2016 | Yau .................... H04L 63/0807 |
| 2016/0328641 A1 | 11/2016 | Alsaud et al. |
| 2016/0342750 A1 | 11/2016 | Alstad et al. |
| 2016/0342751 A1 | 11/2016 | Alstad et al. |
| 2017/0091397 A1 | 3/2017 | Shah et al. |
| 2017/0103164 A1 | 4/2017 | Dunlevy et al. |
| 2017/0103165 A1 | 4/2017 | Dunlevy et al. |
| 2017/0132621 A1* | 5/2017 | Miller ................. G06Q 20/3829 |
| 2017/0351821 A1 | 12/2017 | Tanner et al. |

OTHER PUBLICATIONS

Bhattacharya, Indrajit and Getoor, Lise, *Entity Resolution in Graphs*, Department of Computer Science, University of Maryland (2005) (21 pgs.).

Chen et al., *Adaptive Graphical Approach to Entity Resolution*, Jun. 18-23, 2007, Proceedings of the 7th ACM/IEEE-CS Joint Conference on Digital Libraries, pp. 204-213 (10 pgs.).

Christen, *Data Matching, Concepts and Techniques for Record Linkage, Entity Resolution, and Duplicate Detection*, © Springer-Verlag Berlin Heidelberg, 2012 (279 pgs.).

Cohen et al., *A Comparison of String Metrics for Matching Names and Records*, ©2003, American Association for Artificial Intelligence (www.aaai.org) (6 pgs.).

Coleman et al., Medical Innovation—a diffusion study; The Bobbs-Merrill Company, Inc., 1966 (248 pgs.).

Domingos et al., Mining High-Speed Data Streams, (2000) (10 pgs.).

Greenhalgh et al., Diffusion of Innovations in Health Service Organisations—a systematic literature review, Blackwell Publishing, 2005 (325 pgs.).

Jackson et al., The Evolution of Social and Economic Networks, Journal of Economic Theory 106, pp. 265-295, 2002 (31 pgs.).

Jackson, Matthew O., Social and Economic Networks, Princeton University Press, 2008 (509 pgs.).

Krempl et al., Open Challenges for Data Stream Mining Research, SIGKDD Explorations, vol. 16, Issue 1, Jun. 2014 (64 pgs.).

Lin et al., A simplicial complex, a hypergraph, structure in the latent semantic space of document clustering, © Elsevier, 2005 (26 pgs.).

Mathjax, Naive Bayes Categorisation (with some help from Elasticsearch), blog post dated Dec. 29, 2013 (https://blog.wtf.sg/2013/12/29/naive-bayes-categorisation-with-some-help-from-elasticsearch/). (8 pgs.).

(56) References Cited

OTHER PUBLICATIONS

Newman, Modularity and community structure in networks, PNAS, vol. 103, No. 23, pp. 8581-8582 Jun. 6, 2006 (2 pgs.).
Rebuge, Business Process Analysis in Healthcare Environments, 2011, Ellsevier Ltd., pp. 99-116 (18 pgs.).
Titan Database Documentation ©2015 (disclosed at http://s3.thinkaurelius.com/docs/titan/1.0.0/ (printed Sep. 16, 2016) (214 pgs.).
Wasserman et al., *Social Network Analysis: Methods and Applications*, Cambridge University Press; 1994 (434 pgs.).
White et al., *Algorithms for Estimating Relative Importance in Networks*, Proceedings of the Ninth ACM SIGKDD International Conference on Knowledge Discovery and Data Mining, 2003 (10 pgs.).
Webpage: New Health Care Electronic Transactions Standards Versions 5010, D.0, and 3.0, Jan. 2010 CN 903192; http://www.cms.gov/Regulations-and-Guidance/HIPAA-Adminstrative-Simplification/Versions5010and D0/downloads/w5010BasicsFctCht.pdf (4 pgs.).
Webpage: U.S. Dept. of Health and Human Services, Guidance Regarding Methods for De-identification of Protected Health Information in Accordance with the Health Insurance Portability and Accountability Act (HIPAA) Privacy Rule, http://www.hhs.gov/ocr/privacy/hipaa/understanding/coveredentities/De-identification/guidance.html printed Oct. 15, 2015 (14 pgs.).
Anonymous: "Oauth—Wikipedia", Sep. 23, 2013. Retrieved from the Internet URL:https://en.wikipedia.org/w/index.php?title+oAuth&oldid+574187532 (3 pages).
Version 5010 and D.0, Center for Medicare and Medicaid Services (2 pgs.).
Anonymous: "Oauth" Wikipedia—Retrieved from the Internet URL:https://en.wikipedia.org/wiki/Oauth (8 pgs.).

\* cited by examiner

```
class OffChainHostSystemProxy:

List this.contracts function register(walletAddress):
        this.contracts.append(walletAddress)
        send event RegisterWallet(walletAddress)

function request(senderAddress, requestData):
        send event Request(requestData)

function respondTo(walletAddress, tokenSignature, token):
        if walletAddress IN this.contracts:
            call walletAddress.saveToken(tokenSignature, token)
```

FIGURE 5

```
class OffChainResourceContract:

Address offchain_host_address = None
    Address offchain_host_token = None
    IdArray request_ids[] = None
    StringArray responses[] = None construct OffChainResourceContract(offchain_host_address):
        call self.offchain_host_address.register(self.address)
        self.offchain_host_address = offchain_host_address function verifyTokenSignature(tokenSignature):
        offchain_host_address = recover_signature_address(tokenSignature)
        if offchain_host_address is equal to self.offchain_host_address:
            return True
        else:
            return False function saveToken(tokenSignature, token):
        if verifyTokenSignature(tokenSignature):
            self.offchain_host_token = token function offChainRequest(requestData):
        requestData.correlation_id = new Id
        request_ids.append(requestData.correlation_id)
        call offchain_host_address.request(self.address, requestData)

function offChainResponse(responseData):
        offchain_host_address =
            recover_signature_address(responseData.data_signature)
        if offchain_host_address is NOT equal to self.offchain_host_address:
            return
        if responseData.request.correlation_id NOT IN request_ids:
            return
        self.responses[responseData.request.correlation_id] =
            responseData.response_data
```

FIGURE 6

```
request {
    Uri          request_uri,
    String       request_method,
    String       request_data,
    Byte64       contract_auth_token,
    Timestamp    request_time,
    Id           correlation_id
}
```

FIGURE 10

```
response {
    request      request,
    String       response_data,
    Signature    data_signature
}
```

FIGURE 11

```
request {
    request_uri = "https://pokitdok.com/eligibility",
    request_method = "eligibility",
    request_data = "{
                        'member': {
                            'birth_date': '1970-01-25',
                            'first_name': 'Jane',
                            'last_name': 'Doe',
                            'id': 'W000000000'
                        },
                        'provider': {
                            'first_name': 'JEROME',
                            'last_name': 'AYA-AY',
                            'npi': '1467560003'
                        },
                        'trading_partner_id': 'MOCKPAYER'
                    }",
    contract_auth_token = "d41d8cd98f00b204e9800998ecf8427e",
    request_time = "1471009680",
    correlation_id = "447a48f4-6093-11e6-8b77-86f30ca893d3"
}
```

FIGURE 13

```
response {
    request = {
        request_url = "https://pokitdok.com/eligibility",
        request_method = "eligibility",
        request_data = "{
                        'member': {
                            'birth_date': '1970-01-25',
                            'first_name': 'Jane',
                            'last_name': 'Doe',
                            'id': 'W000000000'
                        },
                        'provider': {
                            'first_name': 'JEROME',
                            'last_name': 'AYA-AY',
                            'npi': '1467560003'
                        },
                        'trading_partner_id': 'MOCKPAYER'
                    }",
        contract_auth_token = "d41d8cd98f00b204e9800998ecf8427e",
        request_time = "1471009600",
        correlation_id = "447a48f4-6093-11e6-8b77-86f30ca893d3"
    },
    response_data = "{
                        'client_id': '<client_id>',
                        'summary': {
                            'deductible': {
                                'individual': {
                                    'in_network': {
                                        'applied': {
                                            'currency': 'USD',
                                            'amount': '16.43'
                                        },
                                        'limit': {
                                            'currency': 'USD',
                                            'amount': '3000'
                                        },
                                        'remaining': {
                                            'currency': 'USD',
                                            'amount': '2983.57'
                                        }
                                    }}}}}",
        data_signature = "aab190b442fda7b22475296053113cea"
}
```

FIGURE 14

SYSTEM AND METHOD FOR CRYPTOGRAPHICALLY VERIFIED DATA DRIVEN CONTRACTS

PRIORITY CLAIMS/RELATED APPLICATIONS

This application claims the benefit under 35 USC 119(e) to and priority under 35 USC 120 to U.S. Provisional Patent Application Ser. No. 62/354,561, filed on Jun. 24, 2016 and entitled "System and Method for Cryptographically Verified Data Driven Contracts", the entirety of which is incorporated herein by reference.

FIELD

The disclosure relates generally to a system and method for cryptography and block chain systems.

BACKGROUND

In order for Blockchain based smart contracts to take action based on real-world inputs or have real-world side-effects (resource actions) there must exist a mechanism to verify the authenticity of smart contract inputs and data accessed in third party systems by a smart contract.

BRIEF DESCRIPTION OF THE DRAWINGS

FIG. 5 illustrates pseudocode for an OffChainHostSystemProxy class proxies events to the off-chain host system for processing;

FIG. 6 illustrates pseudocode for an OffChainResourceContract class that are base functions to be inherited by any smart contract needing off-chain resource access;

FIG. 10 illustrates an example of request data for an interaction between the smart contract and the off-chain host system;

FIG. 11 illustrates an example of the response data for an interaction between the smart contract and the off-chain host system;

FIG. 13 is an example of the request data passed as the parameter to the offChainRequest method in FIG. 6 by the Elgibility Contract in FIG. 12;

FIG. 14 is an example of the response data passed as the parameter to the offChainResponse method in FIG. 6 by the off-chain system for the healthcare transaction processor shown in FIG. 12.

DETAILED DESCRIPTION OF ONE OR MORE EMBODIMENTS

This system and method specifically deals with methodologies concerning Cryptographically Verified Blockchain-based Contract Data Inputs and Off-chain Side-effects. In order for Blockchain based smart contracts to take action based on real-world inputs or have real-world side-effects (resource actions) there must exist a mechanism to verify the authenticity of smart contract inputs and data accessed in third party systems by a smart contract. Given this capability smart contracts which include third-party system inputs and side-effects can then be processed and later verified, thereby maintaining the integrity of the distributed ledger system of the requisite Blockchain-based smart contract.

Figure 1:
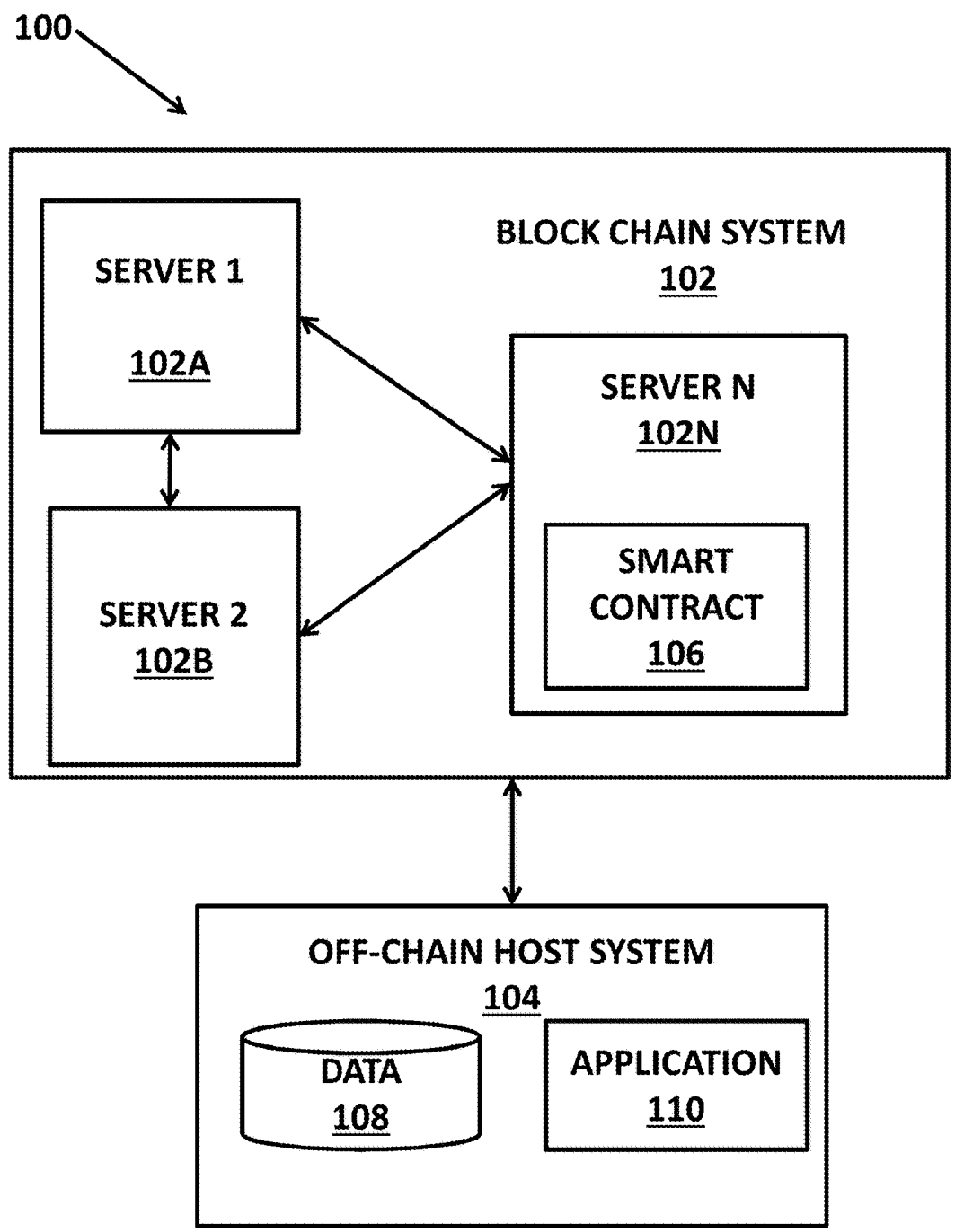
FIG. 1 illustrates an example of a system that includes a block chain system and an off-chain host system.
Figure 2:
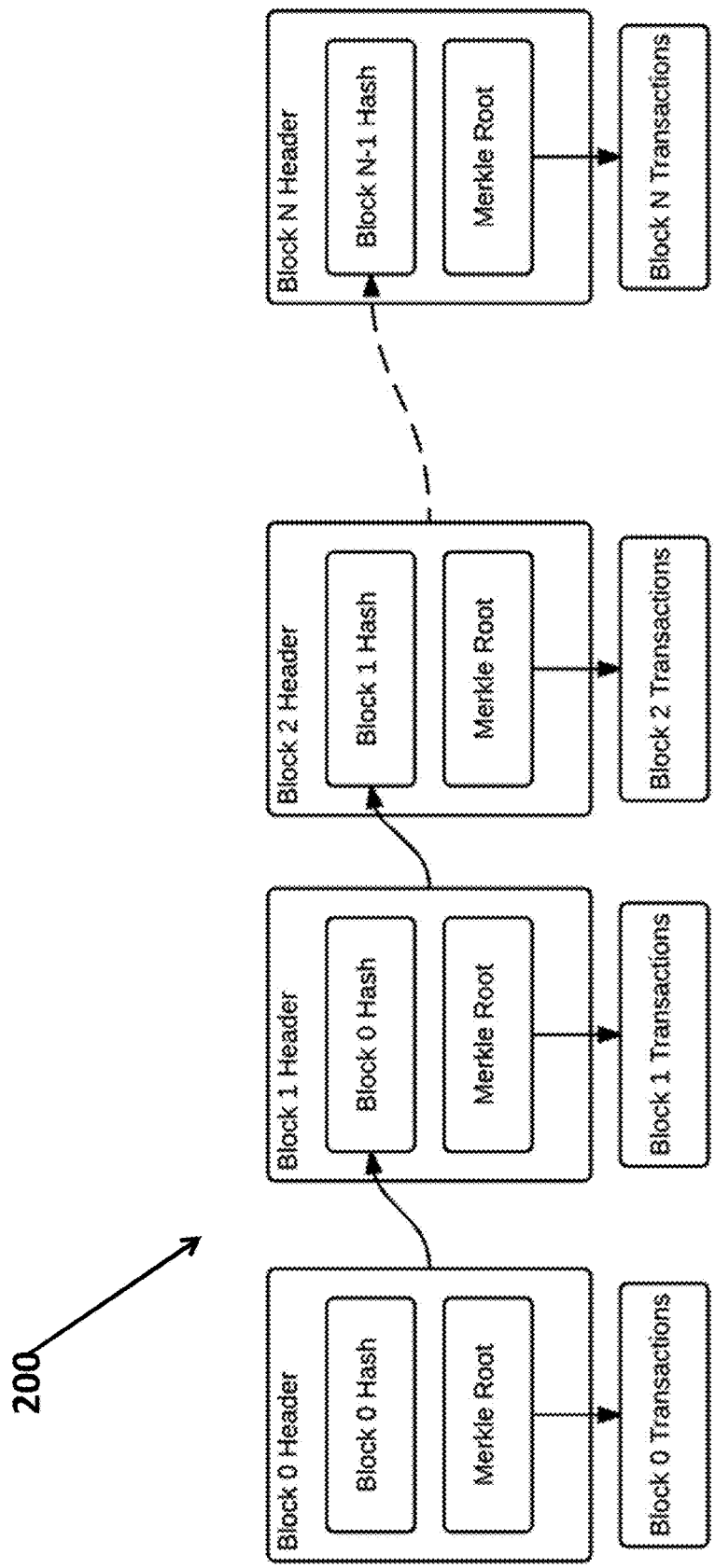
FIG. 2 illustrates an example of the blockchain ledger that is part of the block chain system.
Figure 7:
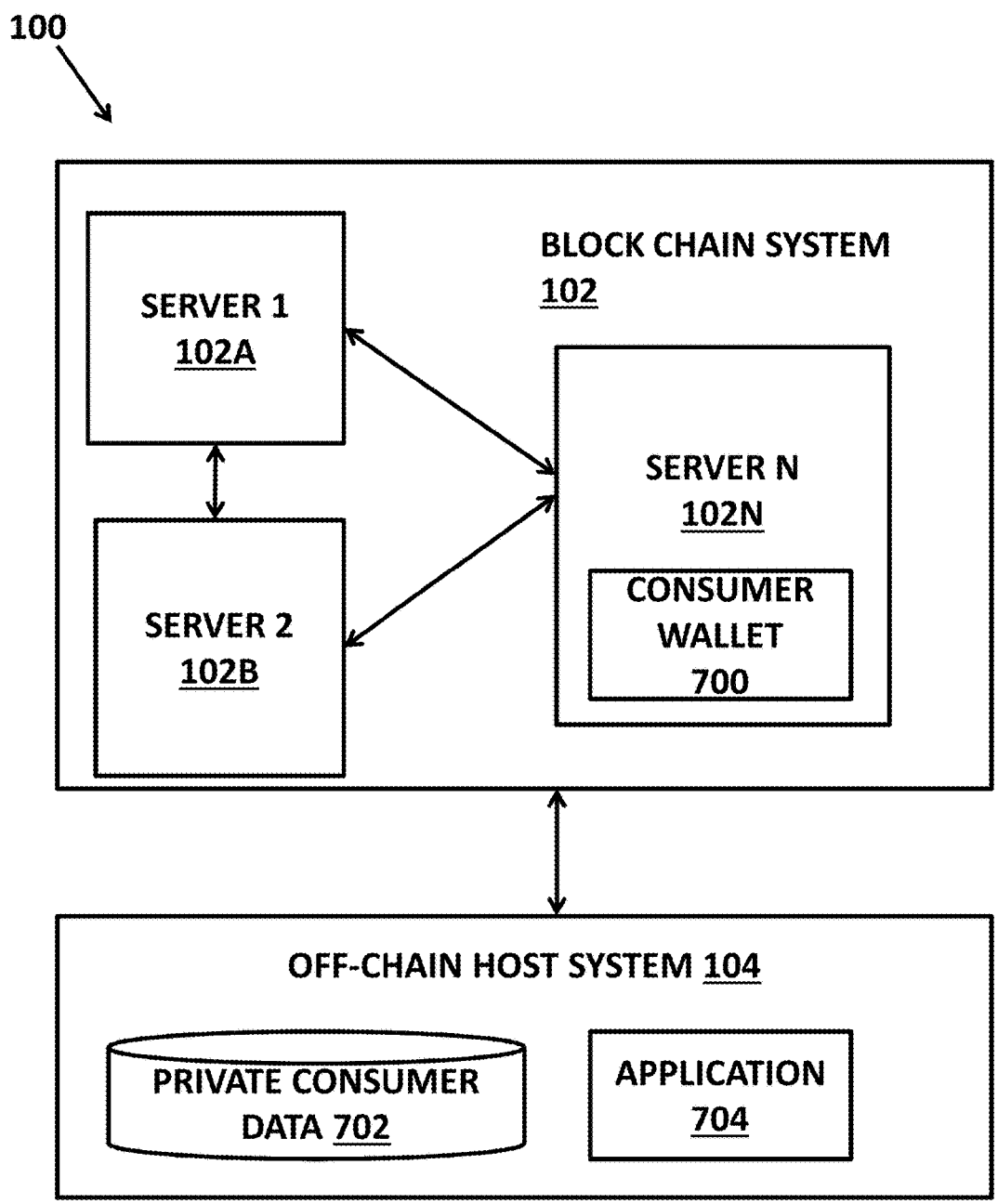
FIG. 7 illustrates an example of the blockchain system and off-chain host being used for a consumer wallet smart contract.
Figure 8:
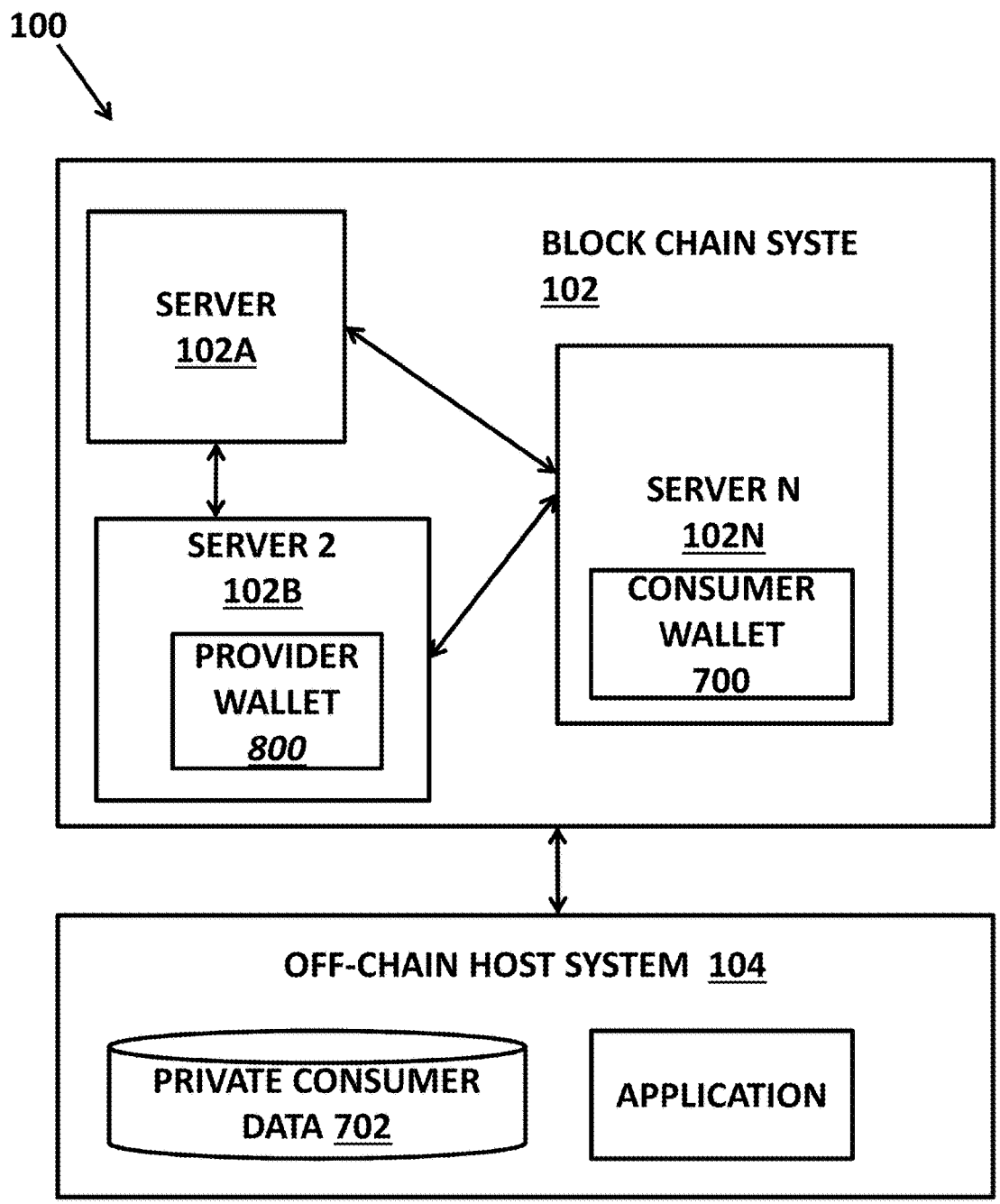
FIG. 8 illustrates an example of the blockchain system and off-chain host being used for a provider wallet smart contract.
Figure 9:
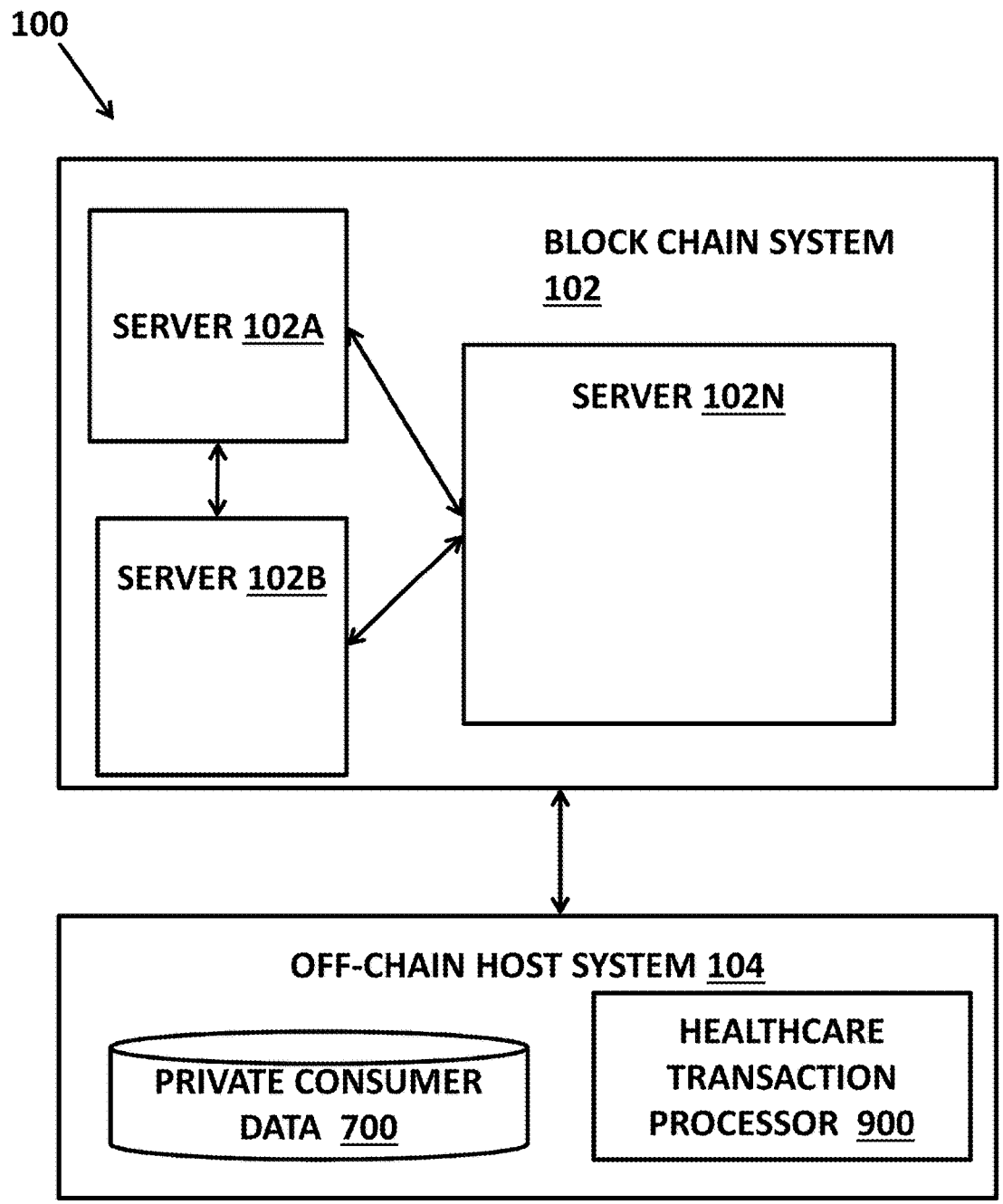
FIG. 9 illustrates an example of the blockchain system and off-chain host being used for healthcare transaction processing.

FIG. 1 illustrates an example of a system 100 that includes a block chain system 102 and one or more off-chain host systems 104 that has a mechanism to verify the authenticity of smart contract inputs and data accessed in third party systems by a smart contract so that blockchain based smart contracts to take action based on real-world inputs or have real-world side-effects (resource actions) using the off-chain host system 104. The block chain system 102 may have one or more computing resources 102, such as one or more server computers 102A, 102B, . . . , 102N as shown in FIG. 1), that are part of the block chain system and host the well-known distributed blockchain ledger system (an example of which is shown in FIG. 2). Each computing resource may include the well known elements that are typically part of a computing resource such as, for example, one or more processors, memory, such as DRAM or SRAM, one or more persistent storage devices, such as flash memory or a hard disk drive, one or more databases, connectivity circuits, etc. that allow the computing resources to communicate with each other over a communications path and to host the blockchain ledger and/or process or generate a block to be appended to the blockchain ledger. For example, the BitCoin monetary system uses blockchain technology and the distributed ledger of the block chain system to provide a monetary system. The blockchain system 102 may further comprise one or more smart contracts 106 hosted on, stored on and/or executed by one or more computing resources 102 that is based on the blockchain ledger of the blockchain system. Each smart contract 106 may be a computerized transaction protocol that executes the terms of a process/protocol or contract in which the smart contract is visible to all users of the blockchain and uses the distributed blockchain ledger. For example, as described below with reference to FIGS. 7-9, the one or more smart contracts may be a consumer healthcare wallet (as shown in FIG. 7), a provider wallet and a consumer wallet (as shown in FIG. 8) or healthcare transaction processor (as shown in FIG. 9).

In the system 100 in FIG. 1, the blockchain system 102 may interact with each off-chain host system 104. Each off-chain host system 104 is a system that is not part of the blockchain system 102 and does not host the distributed blockchain ledger. However, it is desirable to be able to permit the blockchain smart contract to interact with one or more of the off-chain host systems in order to: 1) retrieve data from an off-chain host system (such as third party data inputs); and/or 2) cause real-world side-effects (resource actions) that are carried out by the off-chain host system 104. For example, as described below with reference to FIGS. 7-9 in more detail, the data that is accessed by the smart contract may be private healthcare data of a consumer that is stored/hosted on a third party system that is not part of the blockchain system or healthcare ASC X12N 5010 transaction data that is stored/hosted on a third party system that is not part of the blockchain system. As another example that is below with reference to FIGS. 7-9 in more detail, the resource action may be an action to be taken by a third party system of the off-chain system based on the interaction with the blockchain system 102.

The off-chain system 104 may be implemented using one or more processors, memory, such as DRAM or SRAM, one or more persistent storage devices, such as flash memory or a hard disk drive, one or more databases, connectivity circuits, etc. that allow the off-chain system 104 to store data and host applications and communicate with the blockchain system 102 over a communications path and interact with the smart contract 106. As shown in FIG. 1, the off-chain system 104 may have one or more data stores 108 (implemented in various manners) that may store various data that may be accessed by the smart contract 106 using the system 100. Alternatively or in addition to the one or more data stores 108, the off-chain host system 104 may further have one or more applications/processes 110 resident on the off-chain host system that may perform various processes or acts or operations some of which may be triggered based on a request from the smart contract 106 of the blockchain system 102.

In the system 100, each of the blockchain system 102 and off-chain host system 104 may, in one embodiment, have at least one processor that may be used to execute a plurality of instructions or computer code that implement the methods described below with reference to FIGS. 3-4. In another embodiment, each of the blockchain system 102 and off-chain host system 104 may have one or more pieces of hardware (an integrated circuit, microcontroller, field programmable logic circuit and the like) that implement the methods described below with reference to FIGS. 3-4. Thus, the elements of these systems may be implemented in hardware and/or software. One element of the blockchain system 102 and the off-chain host system 104 may be a transaction manager element that manages the interactions between the smart contract 106 and the off-chain host system 104 including executing the processes shown in FIGS. 3-4. In addition, the transaction manager element may also coordinate the communications and data transfer protocols between the blockchain system 102 and the off-chain host system 104.

The system and method provides a deterministic and cryptographically verifiable chain of transactions, recorded on a blockchain (distributed ledger) system. This system provides an irrefutable public accounting of the transactions involved in incorporating on-chain contract execution with off-chain data and side-effects (resource actions). Thus, the system and method provide a system and method for interaction of smart contracts with off-chain resources as described below.

FIG. 2 illustrates an example of the blockchain ledger 200 that is part of the block chain system 102. The blockchain ledger may have one or more blocks (such as block 0, block 1. Block 3, . . . , block N as shown in FIG. 2. The blockchain thus consists of the blocks that hold timestamped batches of valid transactions. As shown in FIG. 2, each block has a header and each header may include a hash of the prior block in the blockchain, linking the two and a known Merkle root. Each block in the blockchain may also have a body of the block that contains the transactions associated with that particular block. The linked blocks form a chain, with only one (successor) block allowed to link to one other (predecessor) block. In the system 100 described herein, the blockchain may be used to healthcare related data and transactions as described below in more detail with reference to FIGS. 7-9.

Figure 3:
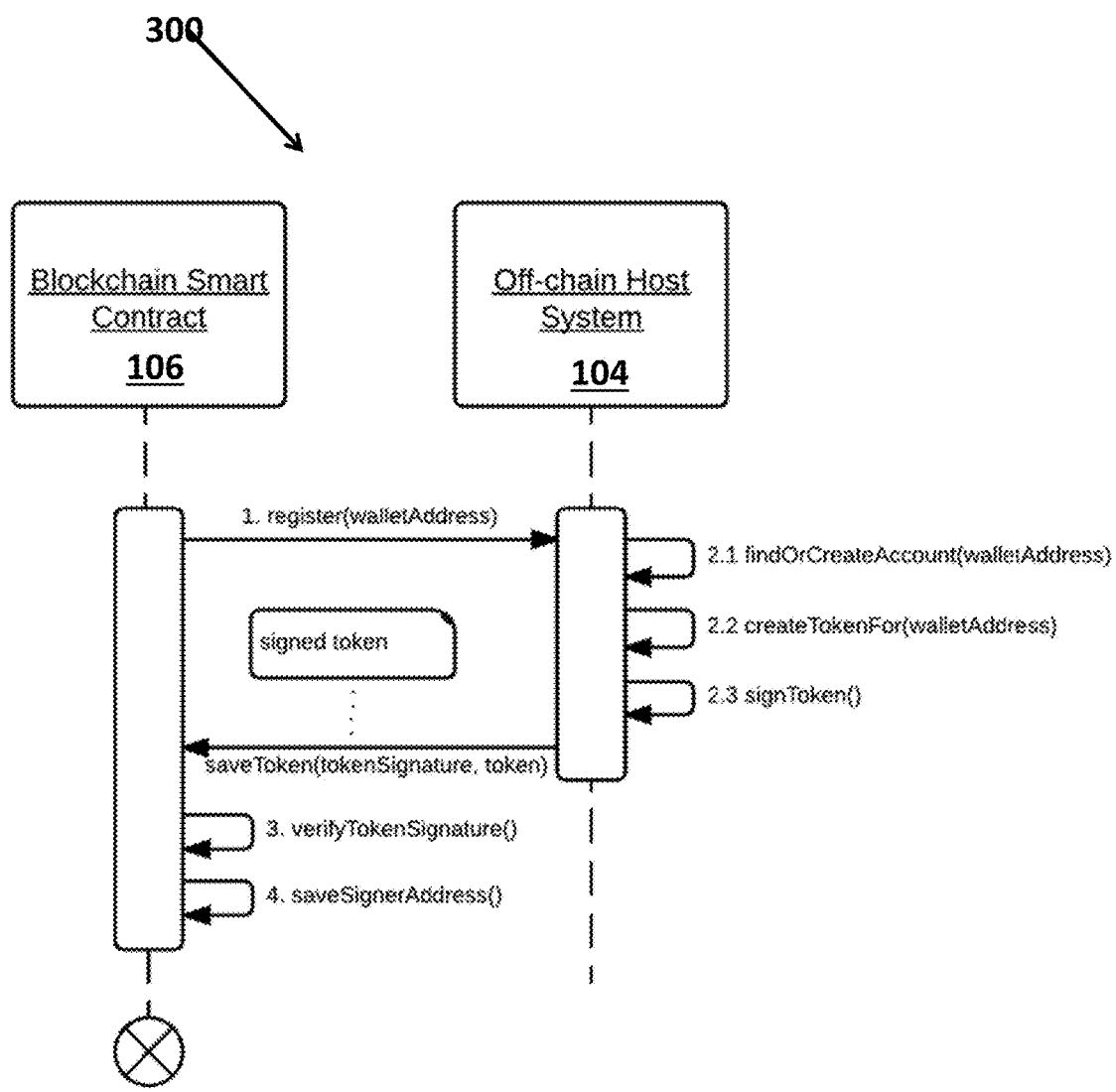
FIG. 3 illustrates an example of a registration method for a smart contract with an off-chain host system in an example in which the smart contract is a consumer wallet.

FIG. 3 illustrates an example of a registration method 300 for a smart contract with an off-chain host system that may be performed, for example, by the system 100 shown in FIG. 1. Specifically, the registration processes shown in FIG. 3 may be performed by the off-chain host system 104 or the blockchain smart contract 106, a combination of both of these systems or by a separate registration element that is coupled to both of the systems. The registration processes shown in FIG. 3 may be implemented in hardware or software. When the registration processes are implemented in software, the registration processes may be a plurality of lines of instructions or computer code that may be executed by a processor associated with the off-chain host system, the blockchain smart contract, a combination of both of these systems or a separate registration system so that the processor is thus configured to perform the registration processes. Alternatively, when the registration processes are implemented in hardware, the registration processes may be performed by a microcontroller, an integrated circuit and the like that perform the processes shown in FIG. 3.

Figure 4:
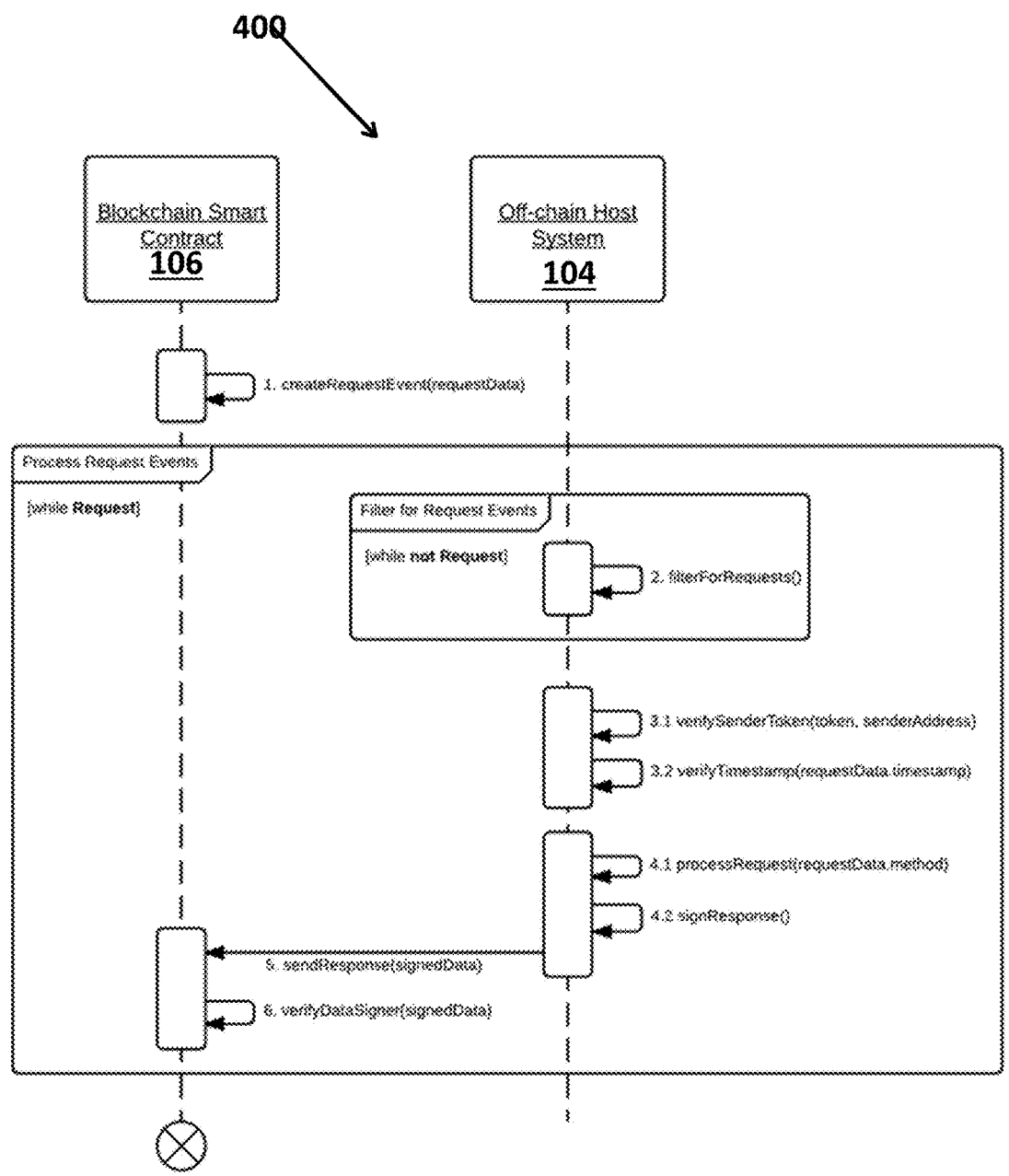
FIG. 4 illustrates an example of a smart contract invocation process of off-chain resources in an example in which the smart contract is a consumer wallet.

In implementing both the registration processes 300 in FIG. 3 and the invocation processes 400 is FIG. 4, the blockchain system 100 may store and then access an OffChainResourceContract piece of code/class (an example of which is shown in FIG. 6) and an OffChainHostSystem Proxy piece of code/class (an example of which is shown in FIG. 5). In one implementation, the smart contract 106 may inherit the functionality of the OffChainResourceContract class.

As shown in FIG. 3, the registration processes 300 may include the smart-contract 106 registering with an off-chain host system 104 by calling an off-chain resource proxy smart-contract (FIG. 5—OffChainHostSystemProxy) method that passes in the address of the smart-contract itself (process 1 in FIG. 3 and register(walletAddress) in FIG. 5 when the smart contract is a consumer wallet use case) and receives via the resource proxy smart-contract (FIG. 5—respondTo(walletAddress, tokenSignature, token)) a unique token that is digitally signed by the off-chain host system 104 to provide data or side-effects. The token and signature are cryptographically verified (process 3 in FIG. 3) by the smart-contract 106 to validate the source of the off-chain access token (FIG. 6—verifyTokenSignature(tokenSignature)).

As part of the registration process shown in FIG. 3, the off-chain host system 104 watches the blockchain transaction log (using a known process that may be performed by the transaction manager element of the off-chain host system 104) for events (such as register (walletAddress) shown in FIG. 3) created by the specific proxy smart-contract representing the off-chain resource. The off-chain host system 104 may then find the off-chain system account associated with the passed in blockchain wallet account address or creates a new off-chain system account and associates the passed in blockchain wallet address with the existing or new off-chain system account (as shown in FIG. 3, process 2.1—findOrCreateAccount(walletAddress)). The off-chain host system 104 may then generate a unique token (as shown in FIG. 3, process 2.2—createTokenFor(walletAddress)) and generate a digital signature of the token using the private key of the blockchain account (address of the proxy smart-contract) associated with the off-chain system (as shown in FIG. 3, process 2.3—signToken( ). The off-chain host system 104 may then store the token with the associated on-chain account address of the requesting smart-contract by invoking the proxy smart-contract with the smart-contract wallet address received, the token signature and the token (as shown in FIG. 5—respondTo(walletAddress, tokenSignature, token)). The proxy smart-contract may then invoke the smart-contract to save the token (as shown in FIG. 3—saveToken(tokenSignature, token) process).

In the registration method shown in FIG. 3, the smart contract 106 may verify the off-chain host system signature (as shown in FIG. 3, process 3 and FIG. 6—verifyTokenSignature(tokenSignature)) and stores the token within the contract (as shown in FIG. 3, process 4—saveSignerAddress( ) and FIG. 6—saveToken(tokenSignature)). In the method, the smart-contract 106 may also store the on-chain wallet address corresponding to the public key used to sign the token (FIG. 6—OffChainResourceContract (offchain_host_address)) which is the address of the proxy smart-contract on the blockchain. Using the above method 300, the smart contract 106 is registered with the off-chain host system 104 so that there is a deterministic and cryptographically verifiable chain of transactions, recorded on a blockchain (distributed ledger) system with irrefutable public accounting of the transactions involved in incorporating on-chain contract execution with off-chain data and side-effects (resource actions).

FIG. 4 illustrates an example of a smart contract invocation process 400 of off-chain resources in an example in which the smart contract is a consumer wallet. The process may be implemented using the same off-chain host system 104 and the blockchain smart contract 106 already described above in FIG. 3. The invocation processes 400 shown in FIG. 4 may be performed by the off-chain host system 104 or the blockchain smart contract 106, a combination of both of these systems or by a separate invocation system or management element that is coupled to both of the systems. The invocation processes shown in FIG. 4 may be implemented in hardware or software. When the invocation processes are implemented in software, the invocation processes may be a plurality of lines of instructions or computer code that may be executed by a processor associated with the off-chain host system, the blockchain smart contract, a combination of both of these systems, a separate invocation system of the transaction manager element so that the processor is thus configured to perform the invocation processes. Alternatively, when the invocation processes are implemented in hardware, the registration processes may be performed by a microcontroller, an integrated circuit and the like that perform the processes shown in FIG. 4.

In the invocation process, the smart contract 106 may publish a transaction targeted to the off-chain host system (as shown in FIG. 4 process 1—createRequestEvent (Requestdata) and FIG. 6—OffChainRequest(requestData)) with a request for data or a side-effect, where the request data (an example of which is shown in FIG. 10) includes the request method itself (must include: requestData.request_uri, and may include: requestData.request_method, and/or requestData.request_data), the contract's token (requestData.contract_auth_token), a timestamp (unixtime, number of seconds since Jan. 1, 1970 UTC, with some number of least significant digits zeroed out, requestData.request_time), and a correlation identifier (a unique identifier, may be a UUID as defined by IETF RFC 4122, requestData.correlation_id). In one embodiment, the request method may be the URI of an idempotent system specific request/response. During the invocation method, the off-chain host system 104 may watch a blockchain transaction log for events (as shown in FIG. 5—Request(senderAddress, requestData) and FIG. 4, process 2—filterForRequests( ) created by the specific proxy smart-contract representing the off-chain resource that was determined by the registration method 300 described above. The off-chain host system 104 may receive the request, verifies that the sender address is associated with the off-chain system account and passed in token in the request (as shown in FIG. 4, process 3.1—verifySenderToken(token, senderAddress), and checks that the timestamp of the request has not been exceeded (as shown in FIG. 4, process 3.2—verifyTimestamp(requestData.request_time)).

Once the off-chain host system 104 has verified that the request is valid, the off-chain host system 104 may satisfy the data request or execute the desired side-effect/action (as shown in FIG. 4, process 4.1—processRequest(requestData.request_method) and generate a response, responseData (an example of which is shown in FIG. 11), which includes the requestData (responseData.request). The off-chain host system 104 may also generate a corresponding digital signature (responseData.data_signature) for the response payload (responseData.response_data) concatenated with the correlation identifier (requestData.correlation_id) of the request using the private key of the blockchain account for the off-chain system (as shown in FIG. 4, process 4.2—signResponse( ). The off-chain host system 104 may then initiate a blockchain transaction (FIG. 4, process 5—sendResponse(signedData) and FIG. 6—offChainResponse(responseData)) targeted to the address of the requesting smart-contract. In the blockchain transaction, the data parameter passed back to the requestor (responseData.response_data) is a use-case specific data element (generated in step 4 shown in FIG. 4 above).

Once the response is received by the smart-contract 106, it may verify that the signature (responseData.data_signature) corresponds to the data (responseData.response_data) and the correlation identifier of the request (responseData.request.correlation_id) and was signed by the key associated with the on-chain wallet address of the off-chain host system (as shown in FIG. 4, process 6—verifyDataSigner (signedData) and FIG. 6—offChainResponse(responseData)). The above method provides a deterministic and cryptographically verifiable chain of transactions, recorded on a blockchain (distributed ledger) system with irrefutable public accounting of the transactions involved in incorporating on-chain contract execution with off-chain data and side-effects (resource actions).

Use Cases

The above described system and method may have many different uses. For example, the system and method may be used for a consumer wallet for personal healthcare information, a provider wallet for healthcare interactions and healthcare ASC X12N 5010 transactions that are each described below in more detail with reference to FIGS. 7-9.

Consumer Wallet for Personal HealthCare Information

A consumer wallet—smart contract on the blockchain—can be built which inherits from OffChainResourceContract class (an example of which is shown in FIG. 6). This wallet can store private information associated with the wallet in the off-chain host system and also provide automated access control to third-party contracts which may need authorization from the consumer to perform healthcare transactions on behalf of the consumer. Additionally, information which the consumer chooses to make public can be stored and made available and access controlled through this wallet.

Figure 12:
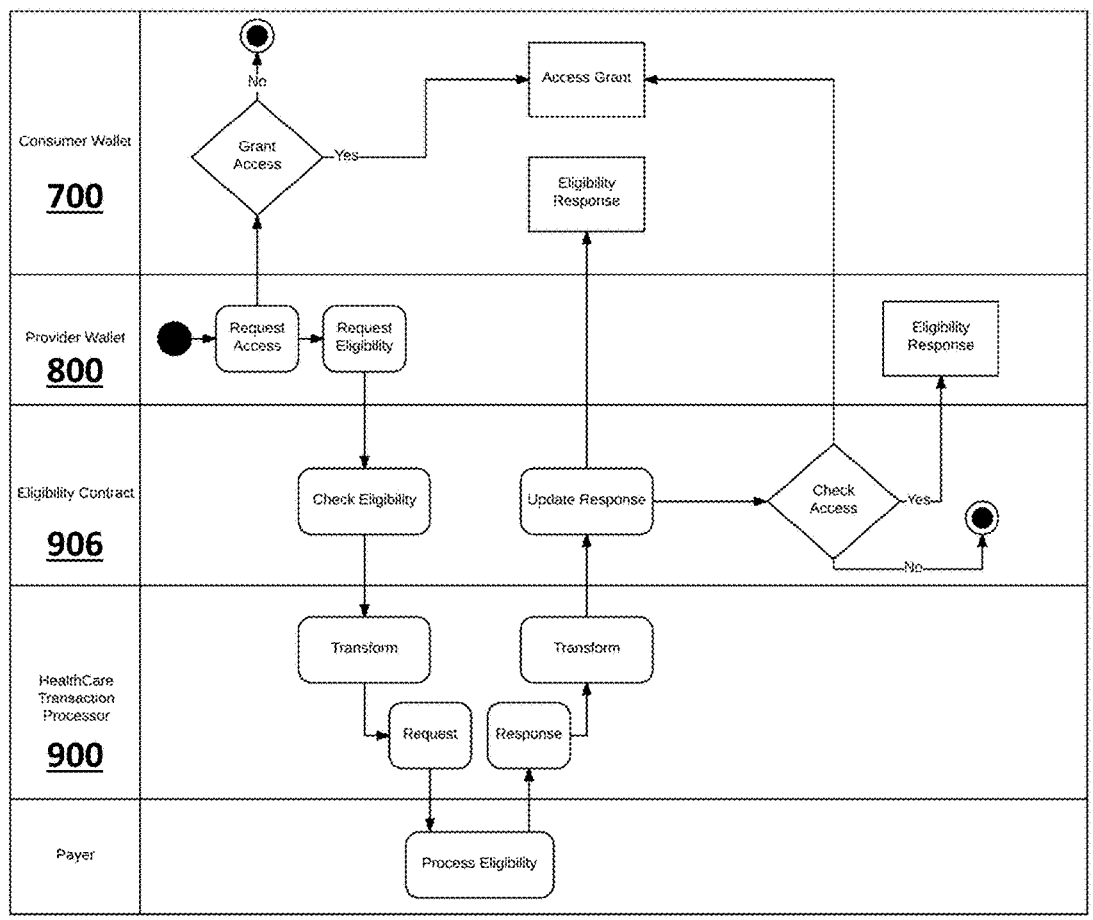
FIG. 12 depicts an implementation where the Consumer Wallet, Provider Wallet and Eligibility Contract are instantiations of the OffChainResourceContract in FIG. 6 implementing the Eligibility (270/271) transaction.

FIG. 7 illustrates an example of the blockchain system 102 and off-chain host 104 being used for a consumer wallet smart contract 700 that is part of the blockchain system 102. When the consumer wallet smart contract 700 is implemented, it may use the method described above to retrieve private healthcare data 702 from the off-chain host system 104 as shown in FIG. 7. FIG. 12 described below depicts an implementation where the Consumer Wallet, Provider Wallet and Eligibility contract are instantiations of the OffChainResourceContract.

Provider Wallet for HealthCare Interactions

A provider wallet can be built which inherits from OffChainResourceContract class. This wallet can be used by the provider to interact with consumer wallet for authorization to access consumer personal health information records, communications and referrals.

FIG. 8 illustrates an example of the blockchain system 102 and off-chain host 104 being used for a provider wallet smart contract 800. When the provider wallet smart contract 800 is implemented, it may use the method described above to retrieve data from the consumer wallet and the consumer private healthcare data from the off-chain host system 104 as shown in FIG. 8. FIG. 12 described below depicts an implementation where the Consumer Wallet, Provider Wallet and Eligibility contract are instantiations of the OffChainResourceContract.

HealthCare ASC X12N 5010 Transactions

The above system and method may be used to process various healthcare ASC X12N 5010 transactions.

FIG. 9 illustrates an example of the blockchain system 102 and off-chain host 104 being used for healthcare transaction processing. In this implementation, a healthcare transaction processor 900 may be implemented on the off-chain host system 104 that processes healthcare transactions off-chain, such as for example, ASC X12N 5010 transactions as described below and shown in the example in FIG. 12.

FIG. 12 depicts an implementation where the Consumer Wallet 700, Provider Wallet 800 and Eligibility smart contract 906 may be instantiations of the OffChainResourceContract (an example of which is shown in FIG. 6) that implement an Eligibility transaction, such as for example a ASC X12N 5010 (270/271) eligibility transaction. As shown in FIG. 12, the consumer wallet 700 may determine and authorize access by the provider wallet 800 and may receive a eligibility response as part of the eligibility method shown in FIG. 12. The provider wallet may request access of the consumer wallet and, once granted access, request eligibility fore the user associated with the consumer wallet and may receive the eligibility response as part of the eligibility method shown in FIG. 12. The eligibility smart contract 906 may perform the eligibility check (based on off-chain resources), update the eligibility response and also check access to the consumer wallet during the eligibility method shown in FIG. 12. In the method, the healthcare transaction processor 900 (which is off-chain and an off-chain resource) may perform various actions as requested by the eligibility smart contract 906 and return a response.

FIG. 13 is an example of the request data passed as the parameter to the offChainRequest method (FIG. 6) by the Elgibility Contract (FIG. 12). FIG. 14 is an example of the response data passed as the parameter to the offChainResponse method (FIG. 6) by the off-chain system (FIG. 12, HealthCare Transaction Processor). The request_data member of the request data structure example shown in FIG. 13 may also be a short resource identifier or reference pointer to off-chain data to limit data storage within the on-chain smart-contract. Similarly, the response_data member of the response data structure example shown in FIG. 14 may also be a short resource identifier or reference pointer to off-chain data to limit data storage within the on-chain smart-contract. Using this pattern and Eligibility Contract example, the system and method may be used to process the following exemplary transactions:

1. Eligibility—The 270/271 transaction set can be processed off-chain and a resource id to the off-chain private information is returned along with other public details of the transaction such as payer details and response times.

2. Claims—The 837 transaction can be processed off-chain and a resource id to the off-chain private information is returned along with other public details of the transaction such as payer details and response times.

3. Enrollment—private and public data controlled through a consumer wallet can be used by third party smart contracts that process real-time healthcare insurance plan enrollment and use this data to accurately calculate risk and match a consumer to an appropriate health insurance plan resulting in an off-chain 834 transaction.

4. Authorization and Referral—using and off-chain 278 transaction and private and public data controlled through a consumer wallet, third party smart contracts that process real-time authorization based on public preferences added to the consumer wallet by the consumer and provider requirements added to the consumer wallet by the referring provider (given consumer consent).

Figure 15:
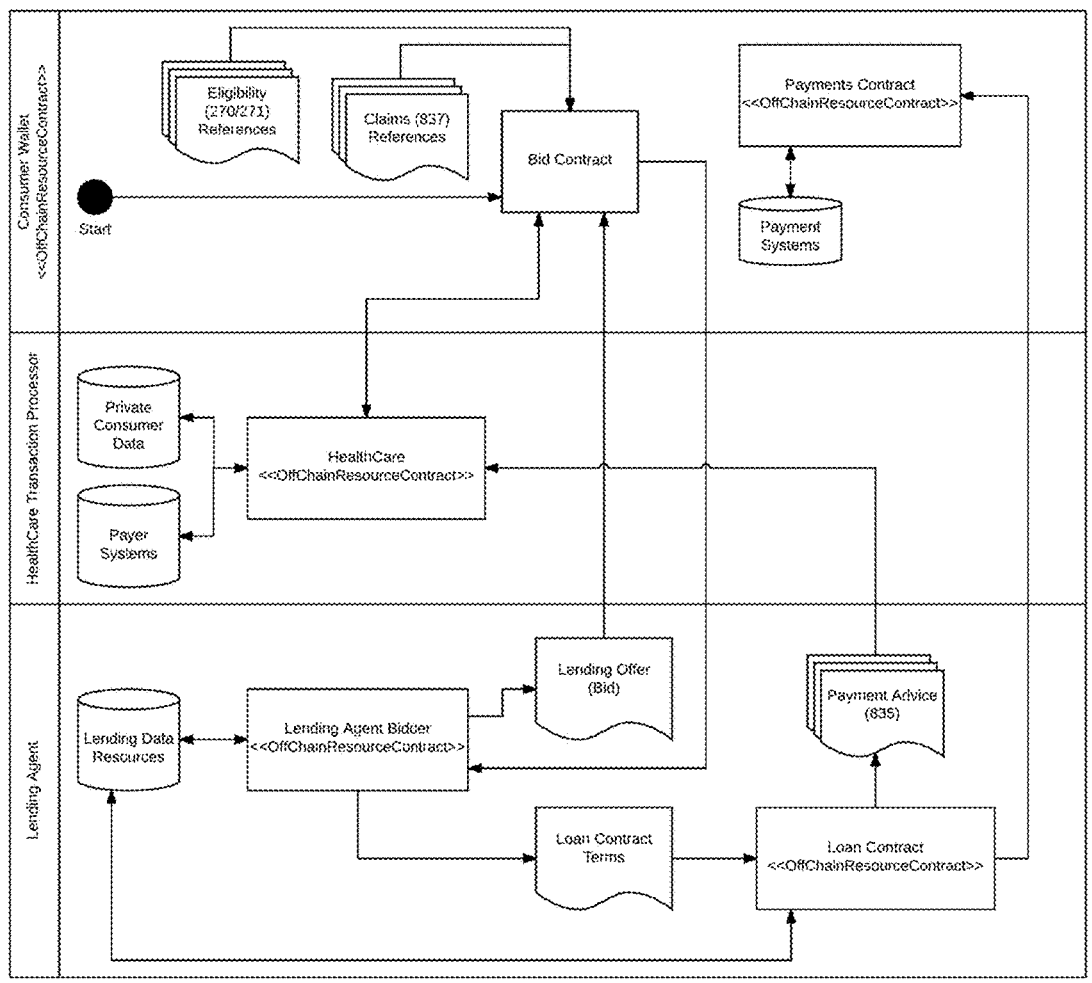
FIG. 15 depicts an implementation in which the Consumer Wallet can initiate a transaction to solicit bids for financing a health care service and incorporate off-chain data from a HealthCare Transaction Processor.

5. Payments and Financing—given the enrollment and claims scenarios above payment can be facilitated by providing public data of the payment and potential funding needs of a consumer for a transaction whereby third-party smart contracts could present loan offers to the consumer wallet for execution by the consumer. FIG. 15 depicts an implementation where the Consumer Wallet can initiate a transaction to solicit bids for financing a health care service and incorporate off-chain data from a HealthCare Transaction Processor. In the implementation, lending Agents, by means of smart contracts implementing the OffChainResourceContract (FIG. 6) for a Lending Agent Bidder and Loan Contract, can bid on and execute a loan respectively and incorporate off-chain data through details provided by interaction with the Consumer Wallet. The Payments Contract implementing the OffChainResourceContract (FIG. 6) managed by the Consumer Wallet can interface with the consumer's off-chain payment system to satisfy payments as part of the loan contract. Finally a health care payment advice (835) contract can be submitted to and serviced by the HealthCare Transaction Processor by means of the HealthCare OffChainResourceContract.

The foregoing description, for purpose of explanation, has been described with reference to specific embodiments. However, the illustrative discussions above are not intended to be exhaustive or to limit the disclosure to the precise forms disclosed. Many modifications and variations are possible in view of the above teachings. The embodiments were chosen and described in order to best explain the principles of the disclosure and its practical applications, to thereby enable others skilled in the art to best utilize the disclosure and various embodiments with various modifications as are suited to the particular use contemplated.

The system and method disclosed herein may be implemented via one or more components, systems, servers, appliances, other subcomponents, or distributed between such elements. When implemented as a system, such systems may include an/or involve, inter alia, components such as software modules, general-purpose CPU, RAM, etc. found in general-purpose computers. In implementations where the innovations reside on a server, such a server may include or involve components such as CPU, RAM, etc., such as those found in general-purpose computers.

Additionally, the system and method herein may be achieved via implementations with disparate or entirely different software, hardware and/or firmware components, beyond that set forth above. With regard to such other components (e.g., software, processing components, etc.) and/or computer-readable media associated with or embodying the present inventions, for example, aspects of the innovations herein may be implemented consistent with numerous general purpose or special purpose computing systems or configurations. Various exemplary computing systems, environments, and/or configurations that may be suitable for use with the innovations herein may include, but are not limited to: software or other components within or embodied on personal computers, servers or server computing devices such as routing/connectivity components, handheld or laptop devices, multiprocessor systems, microprocessor-based systems, set top boxes, consumer electronic devices, network PCs, other existing computer platforms, distributed computing environments that include one or more of the above systems or devices, etc.

In some instances, aspects of the system and method may be achieved via or performed by logic and/or logic instructions including program modules, executed in association with such components or circuitry, for example. In general, program modules may include routines, programs, objects, components, data structures, etc. that perform particular tasks or implement particular instructions herein. The inventions may also be practiced in the context of distributed software, computer, or circuit settings where circuitry is connected via communication buses, circuitry or links. In distributed settings, control/instructions may occur from both local and remote computer storage media including memory storage devices.

The software, circuitry and components herein may also include and/or utilize one or more type of computer readable media. Computer readable media can be any available media that is resident on, associable with, or can be accessed by such circuits and/or computing components. By way of example, and not limitation, computer readable media may comprise computer storage media and communication media. Computer storage media includes volatile and nonvolatile, removable and non-removable media implemented in any method or technology for storage of information such as computer readable instructions, data structures, program modules or other data. Computer storage media includes, but is not limited to, RAM, ROM, EEPROM, flash memory or other memory technology, CD-ROM, digital versatile disks (DVD) or other optical storage, magnetic tape, magnetic disk storage or other magnetic storage devices, or any other medium which can be used to store the desired information and can accessed by computing component. Communication media may comprise computer readable instructions, data structures, program modules and/or other components. Further, communication media may include wired media such as a wired network or direct-wired connection, however no media of any such type herein includes transitory media. Combinations of the any of the above are also included within the scope of computer readable media.

In the present description, the terms component, module, device, etc. may refer to any type of logical or functional software elements, circuits, blocks and/or processes that may be implemented in a variety of ways. For example, the functions of various circuits and/or blocks can be combined with one another into any other number of modules. Each module may even be implemented as a software program stored on a tangible memory (e.g., random access memory, read only memory, CD-ROM memory, hard disk drive, etc.) to be read by a central processing unit to implement the functions of the innovations herein. Or, the modules can comprise programming instructions transmitted to a general purpose computer or to processing/graphics hardware via a transmission carrier wave. Also, the modules can be implemented as hardware logic circuitry implementing the functions encompassed by the innovations herein. Finally, the modules can be implemented using special purpose instructions (SIMD instructions), field programmable logic arrays or any mix thereof which provides the desired level performance and cost.

As disclosed herein, features consistent with the disclosure may be implemented via computer-hardware, software and/or firmware. For example, the systems and methods disclosed herein may be embodied in various forms including, for example, a data processor, such as a computer that also includes a database, digital electronic circuitry, firmware, software, or in combinations of them. Further, while some of the disclosed implementations describe specific hardware components, systems and methods consistent with the innovations herein may be implemented with any combination of hardware, software and/or firmware. Moreover, the above-noted features and other aspects and principles of the innovations herein may be implemented in various environments. Such environments and related applications may be specially constructed for performing the various routines, processes and/or operations according to the invention or they may include a general-purpose computer or computing platform selectively activated or reconfigured by code to provide the necessary functionality. The processes disclosed herein are not inherently related to any particular computer, network, architecture, environment, or other apparatus, and may be implemented by a suitable combination of hardware, software, and/or firmware. For example, various general-purpose machines may be used with programs written in accordance with teachings of the invention, or it may be more convenient to construct a specialized apparatus or system to perform the required methods and techniques.

Aspects of the method and system described herein, such as the logic, may also be implemented as functionality programmed into any of a variety of circuitry, including programmable logic devices ("PLDs"), such as field programmable gate arrays ("FPGAs"), programmable array logic ("PAL") devices, electrically programmable logic and memory devices and standard cell-based devices, as well as application specific integrated circuits. Some other possibilities for implementing aspects include: memory devices, microcontrollers with memory (such as EEPROM), embedded microprocessors, firmware, software, etc. Furthermore, aspects may be embodied in microprocessors having software-based circuit emulation, discrete logic (sequential and combinatorial), custom devices, fuzzy (neural) logic, quantum devices, and hybrids of any of the above device types. The underlying device technologies may be provided in a variety of component types, e.g., metal-oxide semiconductor field-effect transistor ("MOSFET") technologies like complementary metal-oxide semiconductor ("CMOS"), bipolar technologies like emitter-coupled logic ("ECL"), polymer technologies (e.g., silicon-conjugated polymer and metal-conjugated polymer-metal structures), mixed analog and digital, and so on.

It should also be noted that the various logic and/or functions disclosed herein may be enabled using any number of combinations of hardware, firmware, and/or as data and/or instructions embodied in various machine-readable or computer-readable media, in terms of their behavioral, register transfer, logic component, and/or other characteristics. Computer-readable media in which such formatted data and/or instructions may be embodied include, but are not limited to, non-volatile storage media in various forms (e.g., optical, magnetic or semiconductor storage media) though again does not include transitory media. Unless the context clearly requires otherwise, throughout the description, the words "comprise," "comprising," and the like are to be construed in an inclusive sense as opposed to an exclusive or exhaustive sense; that is to say, in a sense of "including, but not limited to." Words using the singular or plural number also include the plural or singular number respectively. Additionally, the words "herein," "hereunder," "above," "below," and words of similar import refer to this application as a whole and not to any particular portions of this application. When the word "or" is used in reference to a list of two or more items, that word covers all of the following interpretations of the word: any of the items in the list, all of the items in the list and any combination of the items in the list.

Although certain presently preferred implementations of the invention have been specifically described herein, it will be apparent to those skilled in the art to which the invention pertains that variations and modifications of the various implementations shown and described herein may be made without departing from the spirit and scope of the invention. Accordingly, it is intended that the invention be limited only to the extent required by the applicable rules of law.

While the foregoing has been with reference to a particular embodiment of the disclosure, it will be appreciated by those skilled in the art that changes in this embodiment may be made without departing from the principles and spirit of the disclosure, the scope of which is defined by the appended claims.

The invention claimed is:

1. A system, comprising:
 a blockchain computer system that stores and maintains a blockchain ledger, the blockchain computer system hosting a smart contract that uses the blockchain ledger to cryptographically verify blockchain-based transactions with the smart contract, off-chain data inputs and off-chain resource actions;
 an off-chain computer system that is not part of the blockchain system and does not store or maintain the blockchain ledger, the off-chain system having one or more of a data store that stores private consumer data about a user whose access is controlled by the user and an application that is configured to perform an off-chain resource action requested by the blockchain smart contract;
 the blockchain computer system having a transaction manager that generates a request for the off-chain computer system from the blockchain smart contract having an authentication token for the smart contract established during a registration process between the off-chain computer system and the smart contract, a timestamp for the request and a correlation identifier that is published to the blockchain ledger, the request being one of a request for off-chain data input and a request for an off-chain resource action;
 the off-chain computer system having a transaction manager that is configured to watch the blockchain ledger for the request from the blockchain computer system, to receive the request from the blockchain smart contract, to verify the token and the timestamp of the request from the blockchain smart contract, to perform, when the token is verified, an action using one of the data store and the application based on the received request from the blockchain smart contract, to respond to the request from the blockchain smart contract with a response payload generated by the performed action and a digital signature for the response payload concatenated with the correlation identifier of the request from the blockchain smart contract, the digital signature signed using a private key of the off-chain computer system and to initiate a blockchain transaction including the response payload and the digital signature on the blockchain ledger targeted to the blockchain smart contract; and
 the blockchain computer system further configured to verify that the digital signature corresponds to the response payload and the correlation identifier in the response matches the correlation identifier in the request from the blockchain smart contract and verifies that the response is properly signed by the private key of the off-chain computer system.

2. The system claim 1, wherein the blockchain smart contract is configured to register with the off-chain computer system.

3. The system of claim 1, wherein the action is one of retrieving a piece of requested data from the data store of the off-chain computer system and performing an action using the application of the off-chain computer system.

4. The system of claim 1, wherein the blockchain smart contract is a healthcare wallet.

5. The system of claim 4, wherein the healthcare wallet is one of a consumer wallet and a provider wallet.

6. The system of claim 1, wherein the application of the off-chain computer system is a healthcare transaction processor that receives a request to process a healthcare transaction from the blockchain smart contract.

7. The system of claim 6, wherein the healthcare transaction is one of an eligibility transaction, a claims transaction, an enrollment transaction, a referral transaction and a payment transaction.

8. A method, comprising:
 providing a blockchain computer system that stores and maintains a blockchain ledger, the blockchain computer system hosting a smart contract that uses the blockchain ledger to cryptographically verify blockchain-based transactions with the smart contract, off-chain data inputs and off-chain resource actions;
 providing an off-chain computer system that is not part of the blockchain system and does not store or maintain the blockchain ledger, the off-chain system having one or more of a data store that stores private consumer data about a user whose access is controlled by the user and an application that is configured to perform an action requested by the blockchain smart contract;
 generating, by the blockchain computer system, a request for the off-chain computer system from the blockchain smart contract having an authentication token for the smart contract established during a registration process between the off-chain computer system and the smart contract, a timestamp for the request and a correlation identifier that is published to the blockchain ledger, the request being one of a request for off-chain data input and a request for an off-chain resource action;

receiving, by the off-chain computer system, the request from the blockchain smart contract;

verifying, by the off-chain computer system, the token and the timestamp of the request from the blockchain smart contract;

performing, by the off-chain computer system when the token is verified, an action using one of the data store and the application based on the received request from the blockchain smart contract;

generating, by the off-chain computer system, a response to the request from the blockchain smart contract with a response payload generated by the performed action and a digital signature for the response payload concatenated with the correlation identifier of the request from the blockchain smart contract, the digital signature signed using a private key of the off-chain computer system;

initiating, by the off-chain computer system, a blockchain transaction including the response payload and the digital signature on the blockchain ledger targeted to the blockchain smart contract; and verifying, by the blockchain smart contract, that the digital signature corresponds to the response payload and the correlation identifier in the response matches the correlation identifier in the request from the blockchain smart contract and that the response is properly signed by the private key of the off-chain computer system.

9. The method of claim 8 further comprising registering the blockchain smart contract with the off-chain computer system.

10. The method of claim 9, wherein registering the blockchain smart contract with the off-chain computer system further comprises sending, by the blockchain smart contract, an address of the blockchain smart contract, creating, by the off-chain computer system, a token for the received address of the blockchain smart contract, signing, by the off-chain computer system, the token and sending, by the off-chain computer system, the signed token to the blockchain smart contract.

11. The method of claim 8, wherein the action is one of retrieving a piece of requested data from the data store of the off-chain computer system and performing an action using the application of the off-chain computer system.

12. The method of claim 8, wherein the blockchain smart contract is a healthcare wallet.

13. The method of claim 12, wherein the healthcare wallet is one of a consumer wallet and a provider wallet.

14. The method of claim 8, wherein the application of the off-chain computer system is a healthcare transaction processor that receives a request to process a healthcare transaction from the blockchain smart contract.

15. The method of claim 14, wherein the healthcare transaction is one of an eligibility transaction, a claims transaction, an enrollment transaction, a referral transaction and a payment transaction.

16. A system, comprising:
a blockchain computer system that stores and maintains a blockchain ledger, the blockchain computer system hosting a smart contract that uses the blockchain ledger to cryptographically verify blockchain-based transactions with the smart contract, off-chain data inputs and off-chain resource actions;

the blockchain smart contract being configured to generate a request for an off-chain computer system having an authentication token for the smart contract established during a registration process between the off-chain computer system and the smart contract, a timestamp for the request and a correlation identifier that is published to the blockchain ledger, the request being one of a request for off-chain data input and a request for an off-chain resource action;

the off-chain computer system having a transaction manager that is configured to watch the blockchain ledger for the request from the blockchain computer system, to receive the request from the blockchain smart contract, to verify the token and the timestamp of the request from the blockchain smart contract, to perform, when the token is verified, an action using one of the data store and the application based on the received request from the blockchain smart contract, to respond to the request from the blockchain smart contract with a response payload generated by the performed action and a digital signature for the response payload concatenated with the correlation identifier of the request from the blockchain smart contract, the digital signature signed using a private key of the off-chain computer system and to imitate a blockchain transaction including the response payload and the digital signature on the blockchain ledger targeted to the blockchain smart contract; and the blockchain computer system further configured to verify the off-chain computer system response based on signed data including verifying that the digital signature corresponds to the response payload and the correlation identifier in the response matches the correlation identifier in the request from the blockchain smart contract and verifies that the response is properly signed by the private key of the off-chain computer system.

17. The system claim 16, wherein the blockchain smart contract is configured to register with the off-chain computer system.

18. The system of claim 16, wherein the action is one of retrieving a piece of requested data from the data store of the off-chain computer system and performing an action using the application of the off-chain computer system.

19. The system of claim 16, wherein the blockchain smart contract is a healthcare wallet.

20. The system of claim 19, wherein the healthcare wallet is one of a consumer wallet and a provider wallet.

* * * * *